(12) United States Patent
Roh

(10) Patent No.: US 9,775,727 B2
(45) Date of Patent: Oct. 3, 2017

(54) WEARABLE ROBOTS AND CONTROL METHODS THEREOF

(71) Applicant: Samsung Electronics Co., Ltd., Suwon-Si, Gyeonggi-Do (KR)

(72) Inventor: Chang-Hyun Roh, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 470 days.

(21) Appl. No.: 14/302,962

(22) Filed: Jun. 12, 2014

(65) Prior Publication Data

US 2015/0088269 A1 Mar. 26, 2015

(30) Foreign Application Priority Data

Sep. 26, 2013 (KR) .................. 10-2013-0114449

(51) Int. Cl.
*A61F 2/72* (2006.01)
*A61H 3/00* (2006.01)

(52) U.S. Cl.
CPC .................. *A61F 2/72* (2013.01); *A61H 3/00* (2013.01)

(58) Field of Classification Search
CPC .... A61H 3/00; A61H 3/008; A61H 2003/001; A61H 2003/007; A61H 2201/165; A61H 2201/5051–2201/5074; A61H 2201/5092–2201/5094; A61H 2230/62–2230/625; A61F 2002/5038–2002/5043; A61F 2002/701; A61F 2002/704; A61F 2002/6872; A61F 2002/74–2002/741; A61F 2/72; A61F 5/00; A61F 5/01; A61F 5/0123–5/0125; A61F 2005/0132–2005/0179
See application file for complete search history.

(56) References Cited

U.S. PATENT DOCUMENTS

| 2008/0242521 A1* | 10/2008 | Einav .................... A61B 5/1116 482/110 |
| 2011/0066088 A1* | 3/2011 | Little ........................ A61F 2/72 601/35 |
| 2013/0006159 A1 | 1/2013 | Nakashima et al. |

FOREIGN PATENT DOCUMENTS

| KR | 101171225 B1 | 8/2012 |
| KR | 101242517 B1 | 3/2013 |

* cited by examiner

*Primary Examiner* — Rachel Young
(74) *Attorney, Agent, or Firm* — Harness, Dickey & Pierce, P.L.C.

(57) ABSTRACT

A wearable robot may comprise: a robot unit including machinery configured to assist a wearer's muscular strength; at least one first sensor provided on the wearer's knees and configured to detect the wearer's motion of pressing the wearer's knees; and/or a controller configured to judge whether or not the wearer intends to stand up based on information detected using the at least one first sensor, and configured to transmit a control signal to assist corresponding muscular strength to the robot unit upon judging that the wearer intends to stand up.

10 Claims, 10 Drawing Sheets

WEARABLE ROBOTS AND CONTROL METHODS THEREOF

CROSS-REFERENCE TO RELATED APPLICATION(S)

This application claims priority from Korean Patent Application No. 10-2013-0114449, filed on Sep. 26, 2013, in the Korean Intellectual Property Office (KIPO), the entire contents of which are incorporated herein by reference.

BACKGROUND

1. Field

Some example embodiments may relate to wearable robots that determine when to provide muscular strength assistance to assist standing-up motion. Some example embodiments may relate to control methods of wearable robots that determine when to provide muscular strength assistance to assist standing-up motion.

2. Description of Related Art

Wearable robots having various purposes, such as assistance to muscular strength during action of handicapped persons, the elderly, and the infirm, rehabilitation of patients with myopathy, assistance to solders equipped with military equipment, and assistance to laborers loaded, are being vigorously developed.

In general, wearable robots to assist muscular strength may include an upper extremity muscular strength assistance robot for behavior of upper extremities and a lower extremity muscular strength assistance robot for behavior of lower extremities. Among these wearable robots, the lower extremity muscular strength assistance robot denotes a robot serving to assist force of wearer's legs to assist walking using human-robot synchronization.

Such a lower extremity muscular strength assistance robot may be driven so as to sense a wearer's intention to walk and to assist corresponding muscular strength. Here, sensing of the wearer's intention to walk may mean sensing of a wearer's intention to start walk or to finish walk, or mean sensing of moving states of the left foot and the right foot.

The wearer's intention to start walking may correspond to a standing-up motion, wearer's intention to finish walking may correspond to a sitting-down motion. The standing-up motion and the sitting-down motion have an action mechanism different from a general walking motion, and thus an assistance strategy different from that applied to the general walking motion needs to be applied to the standing-up motion and the sitting-down motion.

Although some example embodiments will be described with relation to wearable robots for humans and control methods thereof, those skilled in the art will appreciate that some example embodiments may be applied to other types of robots, systems, and control methods, such as wearable robots for animals and control methods thereof, or more general purpose systems and control methods.

SUMMARY

In some example embodiments, a wearable robot may comprise: a robot unit including machinery configured to assist a wearer's muscular strength; at least one first sensor provided on the wearer's knees and configured to detect the wearer's motion of pressing the wearer's knees; and/or a controller configured to judge whether or not the wearer intends to stand up based on information detected using the at least one first sensor, and configured to transmit a control signal to assist corresponding muscular strength to the robot unit upon judging that the wearer intends to stand up.

In some example embodiments, the at least one first sensor may comprise a pressure sensor or on/off button.

In some example embodiments, the robot unit may include a waist wearable unit worn by the wearer at the wearer's waist.

In some example embodiments, the wearable robot may further comprise: at least one second sensor provided on the waist wearable unit and configured to measure a distance between the wearer's hips and a floor.

In some example embodiments, the at least one second sensor may comprise an ultrasonic sensor or an infrared sensor.

In some example embodiments, the controller may be further configured to judge whether or not the wearer intends to stand up based on the information detected using the at least one first sensor, is further configured to measure the distance between the wearer's hips and the floor using the at least one second sensor upon judging that the wearer intends to stand up, and is further configured to transmit the control signal to assist the corresponding muscular strength to the robot unit when the measured distance exceeds a threshold.

In some example embodiments, a control method of a wearable robot may comprise: judging whether or not pressure to a wearer's knees is detected; and/or judging that the wearer intends to stand up and developing assistance to corresponding muscular strength, upon judging that the pressure to the wearer's knees is detected.

In some example embodiments, the control method may further comprise, after the judging whether or not pressure to the wearer's knees is detected: measuring a distance between the wearer's hips and a floor, upon judging that pressure to the wearer's knees is detected; and/or judging whether or not the measured distance exceeds a threshold.

In some example embodiments, a wearable robot assisting a wearer's muscular strength, configured to sense a wearer's intention to stand up by detecting pressure applied to the wearer's knees and to develop assistance to muscular strength corresponding to the sensed wearer's intention to stand up, may comprise: a device configured to detect the pressure applied to the wearer's knees.

In some example embodiments, the wearable robot may comprise at least one first sensor configured to detect the pressure applied to the wearer's knees.

In some example embodiments, the at least one first sensor may comprise a pressure sensor or on/off button.

In some example embodiments, the wearable robot may be further configured to measure a distance between the wearer's hips and a floor when the pressure applied to the wearer's knees is detected, further configured to judge whether or not the measured distance exceeds a threshold, and/or further configured to develop the assistance to muscular strength corresponding to the sensed wearer's intention to stand up upon judging that the measured distance exceeds the threshold.

In some example embodiments, the wearable robot may comprise at least one second sensor configured to measure the distance between the wearer's hips and the floor.

In some example embodiments, the at least one second sensor may comprise an ultrasonic sensor or an infrared sensor.

In some example embodiments, a robot may comprise: a structure configured to assist a wearer's muscular strength; at least one first sensor provided on or near one of the wearer's knees and configured to detect the wearer's motion of pressing on or near the one of the wearer's knees; and/or a controller configured to judge whether or not the wearer intends to stand up based on information detected using the at least one first sensor, and configured to transmit a control signal to assist corresponding muscular strength to the structure upon judging that the wearer intends to stand up.

In some example embodiments, the robot may further comprise: at least one second sensor provided on or near the other one of the wearer's knees and configured to detect the wearer's motion of pressing on or near the other one of the wearer's knees. The controller may be configured to judge whether or not the wearer intends to stand up based on information detected using the at least one first sensor and the at least one second sensor. The controller may be configured to transmit a control signal to assist corresponding muscular strength to the structure upon judging that the wearer intends to stand up.

In some example embodiments, the structure may comprise at least one support frame.

In some example embodiments, the structure may comprise at least one first support frame and at least one second support frame. The at least one first support frame may be operatively connected to the at least one second support frame by a joint.

In some example embodiments, the robot may further comprise: a device to measure an angle between the at least one first support frame and the at least one second support frame.

In some example embodiments, the robot may further comprise: at least one second sensor configured to detect a distance between a portion of the robot and a floor.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Figure 1:
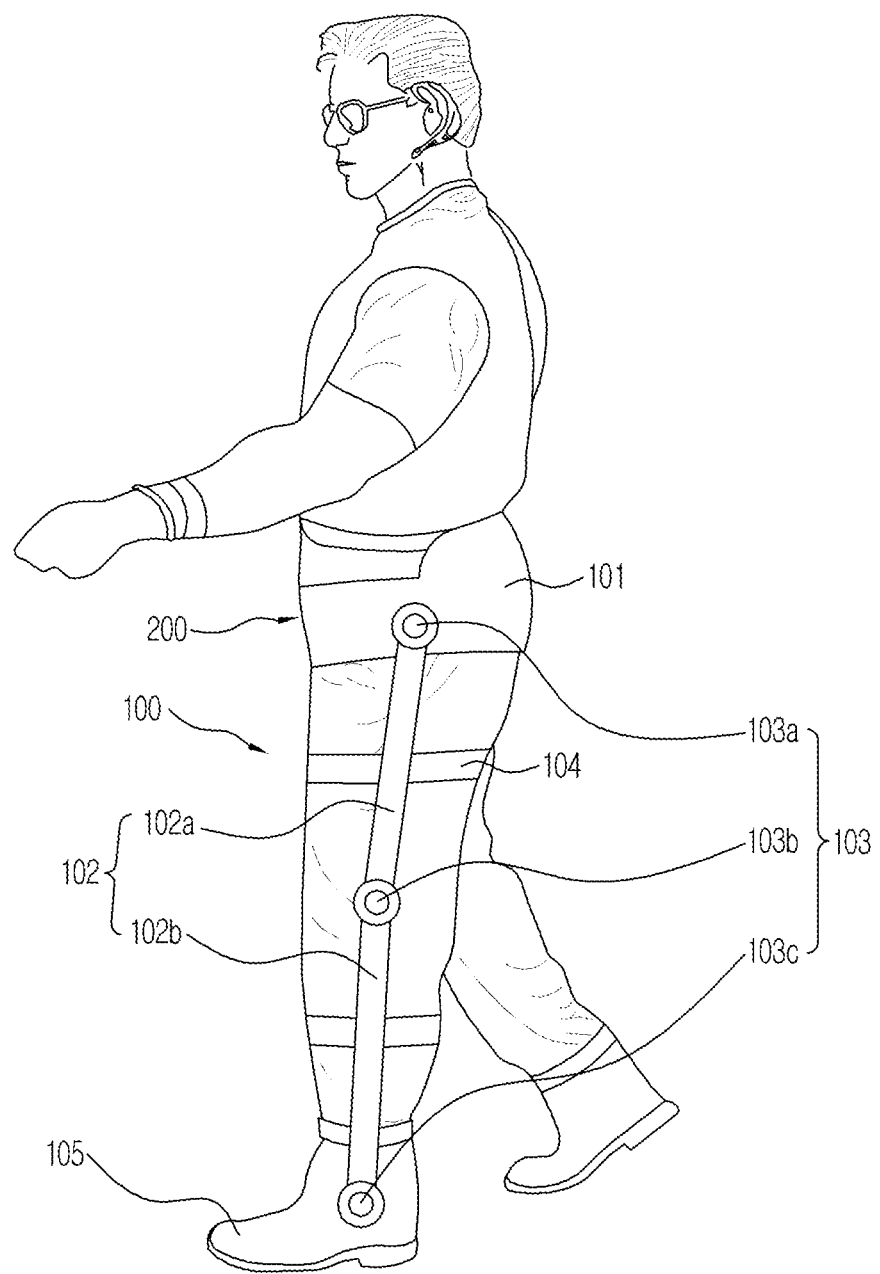
FIG. 1 is a view illustrating the external appearance of a walking assistance robot.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Example embodiments may be described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will typically have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature, their shapes are not intended to illustrate the actual shape of a region of a device, and their shapes are not intended to limit the scope of the example embodiments.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

Hereinafter, a wearable robot in accordance with some example embodiments will be described in detail with reference to the accompanying drawings.

Although some example embodiments will exemplarily describe a walking assistance robot among wearable robots, example embodiments are not limited to the walking assistance robot and may be applied to all wearable robots.

FIG. 1 is a view illustrating the external appearance of a walking assistance robot.

With reference to FIG. 1, a walking assistance robot in accordance with some example embodiments may include a robot unit 100 and a controller 200.

The robot unit 100 is machinery to assist a wearer in walking, and may include joints and motors to perform a walking motion, actuators, such as hydraulic and pneumatic cylinders, and elements, such as belts for coupling with legs. Such a robot unit 100 may assist the wearer's walking motion by operation of the joints and the actuators.

In some example embodiments, the robot unit 100, as exemplarily shown in FIG. 1, includes a waist wearable unit 101, support units 102, joint units 103, and fixing units 104.

The waist wearable unit 101 is worn by the wearer at the waist and may be transformed according to the shape or size of the waist of the wearer, but example embodiments are not limited thereto. Therefore, the waist wearable unit 101 may stably support the waist without deformation according to the wearer's body.

Although not shown in FIG. 1, the waist wearable unit 101 in accordance with some example embodiments may include a waist supporter (not shown) located on the rear surface of the wearer's waist and stably supporting the wearer's waist and a band (not shown) surrounding the wearer's belly.

The waist wearable unit 101 including the band (not shown) and the waist supporter (not shown) may surround the wearer's belly and back at the wearer's waist and belly and thus minimize load applied to the wearer's waist.

In some example embodiments, the controller 200, which will be described later, may be installed on the waist wearable unit 101, but example embodiments are not limited thereto.

The support units 102 serve to support the wearer so that the wearer may walk, and may include a first support frame 102a and a second support frame 102b having designated lengths, as exemplarily shown in FIG. 1. The first support frame 102a and the second support frame 102b may be formed, for example, from flat bar stock, but example embodiments are not limited thereto.

The first support frame 102a may be located on the wearer's upper leg above the wearer's knee. One end of the first support frame 102a may be connected to the above-described waist wearable unit 101, and the other end of the first support frame 102a may be connected to the second support frame 102b. Further, the second support frame 102b may be located on the wearer's lower leg near or above the wearer's knee, and one end of the second support frame 102b may be connected to the first support frame 102a and the other end of the second support frame 102b may be connected to shoe 105.

A connection part between one end of the first support frame 102a and the waist wearable unit 101, a connection part between the other end of the first support frame 102a and one end of the second support frame 102b, and a connection part between the other end of the second support frame 102b and the shoe 105 may be interconnected so that they are rotatable with respect to each other, but example embodiments are not limited thereto.

The respective connection parts may have at least 1 degree of freedom (DOF), but example embodiments are not limited thereto. In some example embodiments, the DOF means a DOF in forward kinematics or inverse kinematics. The DOF of machinery refers to the number of independent movements of the machinery, or the number of variables determining independent movements of respective links at relative positions. For example, an object in a three-dimensional (3D) space formed by the X-axis, Y-axis, and Z-axis has at least one of 3 DOFs to determine the spatial positions of the object (positions of the object at the respective axes), and 3 DOFs to determine the spatial orientations of the object (rotating angles of the object about the respective axes). In some example embodiments, if an object is movable along the respective axes and is rotatable about the respective axes, it may be understood that such an object has 6 DOFs.

In some example embodiments, the first support frame 102a and the second support frame 102b may be adjusted to lengths corresponding to the length of the wearer's leg.

Figure 3:
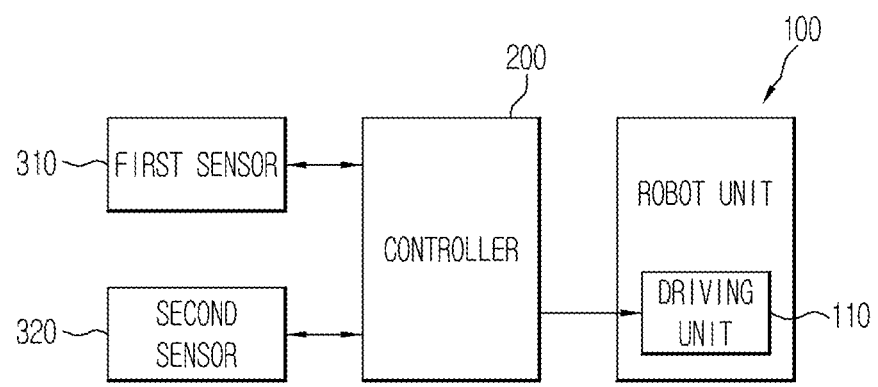
FIG. 3 is a block diagram illustrating the configuration of the walking assistance robot.

The joint units 103, as exemplarily shown in FIG. 3, may include a first joint 103a, a second joint 103b, and a third joint 103c, but example embodiments are not limited thereto.

The first joint 103a is provided at the connection part between one end of the first support frame 102a and the waist wearable unit 101 and serves to execute bending of the thigh with respect to the hip, the second joint 103b is provided at the connection part between the other end of the first support frame 102a and one end of the second support frame 102b and serves to execute bending of the knee, and the third joint 103c is provided at the connection part between the other end of the second support frame 102b and the shoe 105 and serves to execute bending of the ankle.

Although not shown in FIG. 1, a driving unit 110 (with reference to FIG. 3) may be provided on each of the first joint 103a and the second joint 103b.

The driving units 110 transmit driving force for rotation to each of the first joint 103a and the second joint 103b.

For example, the driving units 110 may include a pair of gears (not shown) provided at each connection part and a driving motor (not shown) connected to an axis of one of the pair of gears and driven by an electrical signal transmitted from the controller 200 (with reference to FIG. 3), but example embodiments are not limited thereto. That is, instead of the driving motor (not shown), a hydraulic or pneumatic method may be used.

The first support frame 102a and the second support frame 102b may move with respect to the waist, the knee, and the foot by driving force transmitted from the driving units 110. Thereby, the thigh may be bent with respect to the hip, and the knee and the ankle may be bent.

In some example embodiments, although not shown in FIG. 1, a detection unit (not shown) to detect a joint angle may be provided on each of the first joint 103*a* and the second joint 103*b*, but example embodiments are not limited thereto. In some example embodiments, the detection unit may employ an encoder or a potentiometer, but example embodiments are not limited thereto. In some example embodiments, the detection unit may be provided on the driving motor (not shown) of the driving unit 110.

The fixing units 104 serve to fix the first support frame 102*a* and the second support frame 102*b* to the wearer's leg, and may be bends or belts, but example embodiments are not limited thereto. By fixing the first support frame 102*a* and the second support frame 102*b* to the upper leg and lower leg above and below the knee through the fixing units 104, the moving first support frame 102*a* and second support frame 102*b* may stably assist muscular strength of the wearer's leg.

In some example embodiments, the robot unit 100 in accordance with some example embodiments may further include shoes 105. The shoes 105 surround the wearer's feet and may judge a walking state of the wearer. A pressure sensor (not shown) may be installed at a part of the inside of the shoes 105 contacting the sole of the wearer's foot or be installed at the outer bottom surface of the shoes 105, but example embodiments are not limited thereto.

In some example embodiments, the shoes 105, as exemplarily shown in FIG. 1, serve to surround the wearer's foot to protect the wearer's foot and to measure the walking state of the wearer, and the side surface of the shoes 105 may be rotatably combined with the other end of the second support frame 102*b*, as described above.

In some example embodiments, the upper part of the shoes 105 combined with the second support frame 102*b* is connected to the driving motor (not shown) of the driving unit 110 of the second joint 103*b* using a wire and, thus, the bending angle of the ankle may be determined according to an angle varied by driving of the driving motor (not shown).

Therefore, the shoes 105 judge left and right walking stages of the wearer based on pressure values measured through the above-described pressure sensors (not shown), and transmit the judged left and right walking stages to the controller 200. Thus, the shoes 105 may measure a wearer's walking state and adjust the bending angles of the ankles by the wires during change according to driving of the driving motors (not shown) so that the wearer may stably walk.

In some example embodiments, the shoes 105 may be formed in a one touch-type fixing structure in which a fastening unit (not shown), such as a velcro fastener, a snap fastener, etc., is installed at the upper portion of the shoes 105 so that the wearer may easily and conveniently put on and take off the shoes 105.

In some example embodiments, the robot unit 100 in accordance with some example embodiments may further include a power unit (not shown) to supply power. The power unit may be a battery, but example embodiments are not limited thereto.

In some example embodiments, the walking assistance robot in accordance with some example embodiments may further include a sensor unit which will be described later. In some example embodiments, the sensor unit may include first sensors 310 (with reference to FIG. 3) and second sensors 320 (with reference to FIG. 3). The number of first sensors 310 may be one or more. Similarly, the number of second sensors 320 may be one or more.

In some example embodiments, the first sensors 310 are provided on or near the wearer's knees and serve to detect a motion of putting one hand or two hands on or near the knee or the knees before the wearer performs a rising motion. Such the first sensors 310 may employ a pressure sensor or an on/off button, but example embodiments are not limited thereto. That is, any sensor which may measure pressing may be used as the first sensors 310.

In some example embodiments, the second sensor 320 is provided at the lower portion of the waist supporter (not shown) of the waist wearable unit 101 located on the rear surface of the waist of the wearer and serves to measure a distance between a floor and the wearer's hips. Such second sensors 320 may employ an ultrasonic sensor or an infrared sensor, but example embodiments are not limited thereto. That is, any sensor which may measure a distance may be used as the second sensor 320.

As discussed above, the external appearance of the walking assistance robot in accordance with some example embodiments has been briefly described. Hereinafter, respective elements of the walking assistance robot will be described.

FIG. 3 is a block diagram illustrating the configuration of the walking assistance robot.

With reference to FIG. 3, the walking assistance robot in accordance with some example embodiments may include the first sensors 310, the second sensors 320, the controller 200, and the robot unit 100.

The first sensors 310 are provided on or near the wearer's knees and serve to detect a wearer's motion of pressing on or near the knee or the knees with both hands or one hand before the wearer performs the standing-up motion, as described above.

In general, when a person performs the standing-up motion, the person tends to bend the upper body forward. That is, as exemplarily shown in FIG. 2, the person may bend the upper body forward (state ②) under a sitting state ①, lift the hips (state ③), extend the legs (state ④), and then completely stand (state ⑤). As described above, when a person in the sitting state performs the standing-up motion, the person first bends the upper body forward. If the person bends the upper body forward, the person puts first the hands on or near the knees and supports the body with the arms. That is, the person may stand up while pressing on or near the knees with the arms.

Thereby, in some example embodiments, in order to detect a point of time when the person stands up, a motion of pressing on or near the knees is detected.

The wearable walking assistance robot in accordance with some example embodiments is worn by a human and thus acts as a part of the human body. Therefore, the intention of the wearer wearing the walking assistance robot needs to be accurately understood. For example, if the robot starts walking under the condition that the wearer is not ready to start walking, the wearer may be startled or fall down. On the other hand, if the wearer starts walking but the robot does not sense it and is not operated or starts walking after some delay, the wearer may experience discomfort. Therefore, communication between the walking assistance robot and a person (i.e., the wearer) is considerably important.

In some example embodiments, the above-described wearer's intention may include an intention to stand up, an intention to sit down, or an intention to walk. Since the action mechanism of the 'standing-up' and 'sitting-down' motions is different from that of the 'walking' motion, a muscular assistance strategy differing from that of the 'walking' motion needs to be applied to the 'standing-up' and 'sitting-down' motions.

In some example embodiments, when the wearer wants to perform the 'sitting-down' or 'standing-up' motion, adductor longus (AL) muscles and rectus femoris (RF) muscles of the front portions of the thighs and the gluteus maximus (GM) muscles and biceps femoris (BF) muscles of the back portions of the thighs expand or contract. On the other hand, when the wearer performs the 'walking' motion, different regions expand or contract. Therefore, when the wearer performs the 'sitting-down' or 'standing-up' motion and the 'walking' motion, motion of different regions of the wearer's body are assisted.

Accordingly, the walking assistance robot may include various sensing units to detect the respective intentions.

In some example embodiments, the first sensors 310 are provided on or near the wearer's knees and may detect the intention to perform the 'standing-up' motion among the above-described wearer's intentions.

Conventionally, in order to detect the wearer's intention to stand up, a method in which sensors to measure force are mounted on the soles of the feet and sense magnitude change or position change of ground reaction force is used. However, in order to detect position change of ground reaction force, sensors need to be mounted at plural positions of the soles of the feet, and resolution of the sensors may be insufficient. Further, if the magnitude of ground reaction force is used, measured values may not be clear according to sitting poses.

Therefore, in some example embodiments, in consideration of the fact that, when a person stands up, the person presses on or near the knees with the arms while bending the upper part down, as described above, the first sensors 310 to detect the motion of pressing on or near the knees are provided.

In some example embodiments, the first sensor 310 may be a pressure sensor or an on/off button, but example embodiments are not limited thereto. That is, the first sensor 310 may employ any measurement sensor which may detect a pressing motion.

Figure 4A:
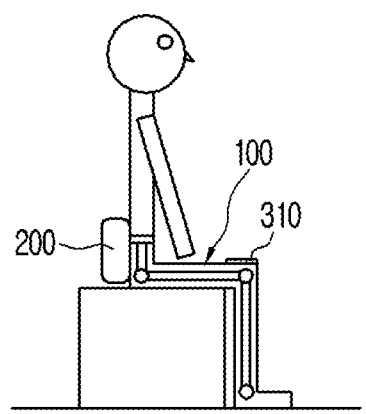
FIGS. 4A and 4B are views illustrating detection of wearer's standing-up time in accordance with some example embodiments.
Figure 4B:
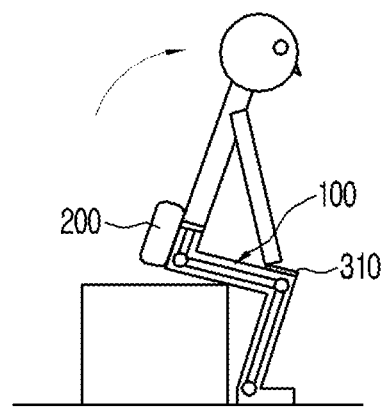
Figure 5A:
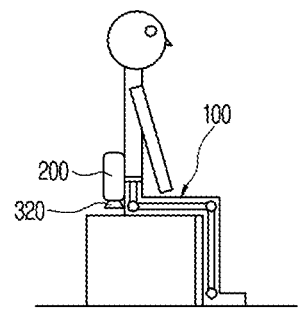
FIGS. 5A and 5B are views illustrating detection of wearer's standing-up time in accordance with some example embodiments.
Figure 5B:
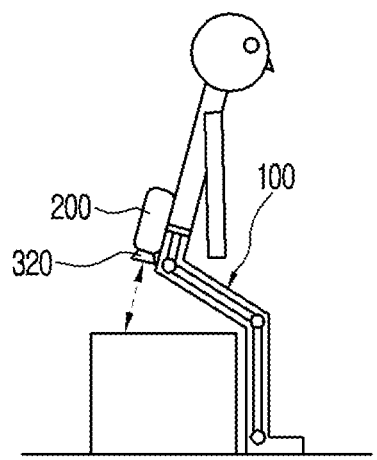

For example, as exemplarily shown in FIGS. 4A and 4B, the first sensors 310 provided on or near the wearer's knees may detect a point of time when the wearer presses on or near the knees with the arms while bending the upper part in the direction of an arrow when the wearer performs the standing-up motion, thus accurately detecting the wearer's intention to stand up. For this purpose, the first sensors 310 may provide detected information to the controller 200.

The second sensor 320 is provided at the lower portion of the waist supporter (not shown) of the waist wearable unit 101 located on the rear surface of the waist of the wearer and serves to measure a distance between the floor and the wearer's hips when the wearer performs the standing-up motion.

Figure 2:
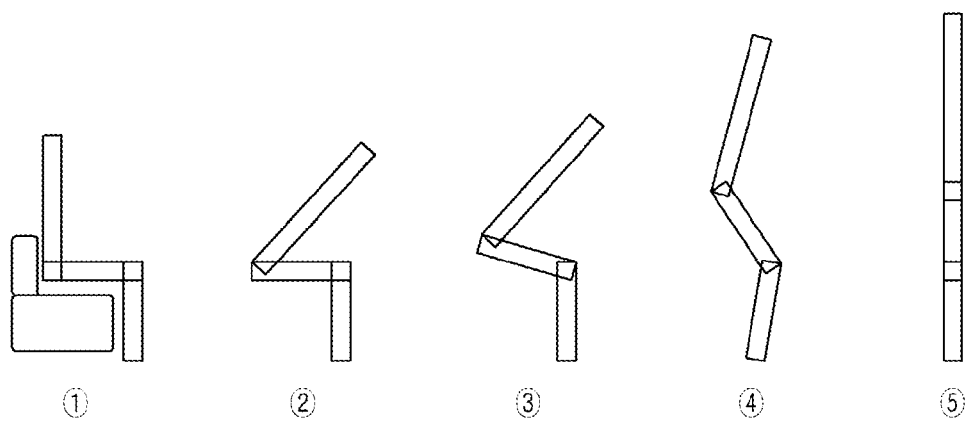
FIG. 2 is a conceptual view sequentially illustrating a wearer's standing-up motion.

As exemplarily shown in FIG. 2, when a person performs the standing-up motion, the person bends the upper body forward (state ②) under the sitting state ①, then lifts the hips (state ③). That is, when the person in the sitting state stands up, the hips are first separated from the floor.

Therefore, in some example embodiments, the second sensor 320 to measure the distance between the floor and the wearer's hips is provided at the lower portion of the rear surface of the waist wearable unit 101 surrounding the wearer's waist, and may accurately detect the wearer's intention to stand up by measuring the distance between the floor and the wearer's hips. For this purpose, the second sensor 320 may provide detected information to the controller 200.

In some example embodiments, the second sensor 320 may be an ultrasonic sensor or an infrared sensor, but example embodiments are not limited thereto. That is, the second sensor 320 may employ any sensor which may detect a distance.

In some example embodiments, each of the above-described first sensors 310 and second sensors 320 may be provided or both the above-described first sensors 310 and second sensors 320 may be provided, but example embodiments are not limited thereto.

In some example embodiments, although FIG. 3 illustrates only the above-described first sensors 310 and second sensors 320, sensors included in the walking assistance robot in accordance with example embodiments are not limited thereto. For example, the walking assistance robot may further include pressure sensors provided on the soles of the shoes 105 to measure ground reaction force, joint angle measurement sensors provided at the first joints 103a and/or the second joints 103b of the robot unit 100, and a tilt sensor provided at the wearer's waist to measure the tilt of the wearer's upper body.

The controller 200 may control the overall operation of the walking assistance robot.

That is, the controller 200 may judge the wearer's intention based on information sensed by the above-described first sensors 310 or second sensors 320, and drive the robot unit 100 according to a result of judgment. In some example embodiments, the above-described wearer's intention may include the intention to stand up, the intention to sit down, or the intention to walk, but example embodiments are not limited thereto.

In some example embodiments, the controller 200 may control the driving units 110 so as to generate different driving forces based on the respective intentions. For example, upon judging that the wearer's intention is the intention to stand up, the controller 200 may transmit a first control signal to the driving units 110 to drive the driving motors (not shown) and thus provide first driving force to assist muscular strength corresponding to such an intention to the joint units 103. Further, upon judging that the wearer's intention is the intention to sit down, the controller 200 may transmit a second control signal to the driving units 110 and thus provide second driving force to assist muscular strength corresponding to such an intention to the joint units 103, and, upon judging that the wearer's intention is the intention to walk, the controller 200 may transmit a third control signal to the driving units 110 and thus provide third driving force to assist muscular strength corresponding to such an intention to the joint units 103.

For this purpose, the controller 200 judges the wearer's intention based on the information provided from the first sensors 310 and the second sensors 320.

As described above, the walking assistance robot in accordance with some example embodiments may include only the first sensors 310, include only the second sensors 320, or include both the first sensors 310 and the second sensors 320. As also described above, the number of first sensors 310 may be one or more, and/or the number of second sensors 320 may be one or more.

Thereby, the controller 200 may judge the wearer's intention to stand up using the information provided from the first sensors 310, judge the wearer's intention to stand up using the information provided from the second sensors 320, or judge the wearer's intention to rise using the information provided from both the first sensors 310 and the second sensors 320.

For example, when the first sensors 310 detect the wearer's knee pressing motion and provides corresponding information to the controller 200, the controller 200 may judge that the wearer intends to perform the 'standing-up' motion at present based on the information transmitted from the first sensors 310, and transmit the first control signal to assist muscular strength corresponding to the 'standing-up' motion to the driving units 110.

When the second sensor 320 measures a distance between the wearer's hips and the floor and provides the measured distance to the controller 200, the controller 200 may judge whether or not the distance transmitted from the second sensor 320 exceeds a desired value (that may or may not be predetermined), judge that the wearer intends to perform the 'standing-up' motion at present upon judging that the distance exceeds the desired value (that may or may not be predetermined), and transmit the first control signal to assist muscular strength corresponding to the 'standing-up' motion to the driving units 110.

Otherwise, when the first sensors 310 detect the wearer's knee pressing motion and provides corresponding information to the controller 200, the controller 200 transmits a command signal to measure a distance between the wearer's hips and the floor to the second sensor 320. Thereafter, when the second sensor 320 measures the distance between the wearer's hips and the floor according to the command signal transmitted from the controller 200 and provides the measured distance to the controller 200, the controller 200 may judge whether or not the distance transmitted from the second sensor 320 exceeds a desired value (that may or may not be predetermined), judge that the wearer intends to perform the 'standing-up' motion at present upon judging that the distance exceeds the desired value (that may or may not be predetermined), and transmit the first control signal to assist muscular strength corresponding to the 'standing-up' motion to the driving units 110.

The robot unit 100 is machinery to assist a wearer in walking, and may include joints and motors to perform the walking motion, actuators, such as hydraulic and pneumatic cylinders, and elements, such as belts, for coupling with the wearer's legs. Such a robot unit 100 may assist the walking motion of the wearer by operation of the joints and the actuators.

Although not shown in FIG. 3, the robot unit 100 may include the waist wearable unit 101, the support units 102, the joint units 103, the fixing units 104, the shoes 105, and the driving units 110, as described above, but example embodiments are not limited thereto. The respective elements have been described above, and a detailed description thereof will thus be omitted.

Further, although not shown in FIG. 3, the robot unit 100 may further include a mode conversion unit (not shown).

The mode conversion unit (not shown) serves to select one of a walking mode, a pose mode, a walking speed, etc. In some example embodiments, the mode conversion unit (not shown) may include a walking mode conversion unit (not shown) to select a walking mode on a flat road surface, a rough road surface, or a stairway, a pose mode conversion unit (not shown) to select a pose, such as sitting down, standing-up, a pose on a tilted surface, and a walking speed conversion unit (not shown) to select a walking speed, such as high, low, and medium, but example embodiments are not limited thereto.

As above, the configuration of the walking assistance robot in accordance with some example embodiments has been described. The walking assistance robot in accordance with some example embodiments may include the first sensors to detect pressing on or near the wearer's knees, and actively sense a point of time when the wearer's intention to stand up is generated and thus accurately determine when to provide muscular strength assistance.

Hereinafter, walking assistance robot control methods in accordance with some example embodiments will be described.

Figure 6:
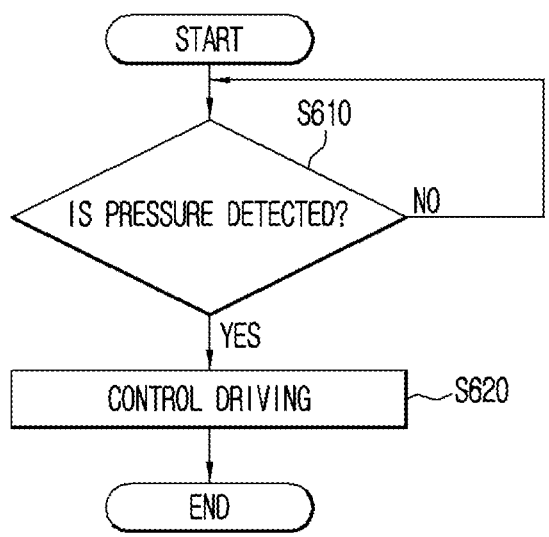
FIG. 6 is a flowchart sequentially illustrating a control method of a walking assistance robot in accordance with some example embodiments.
Figure 7:
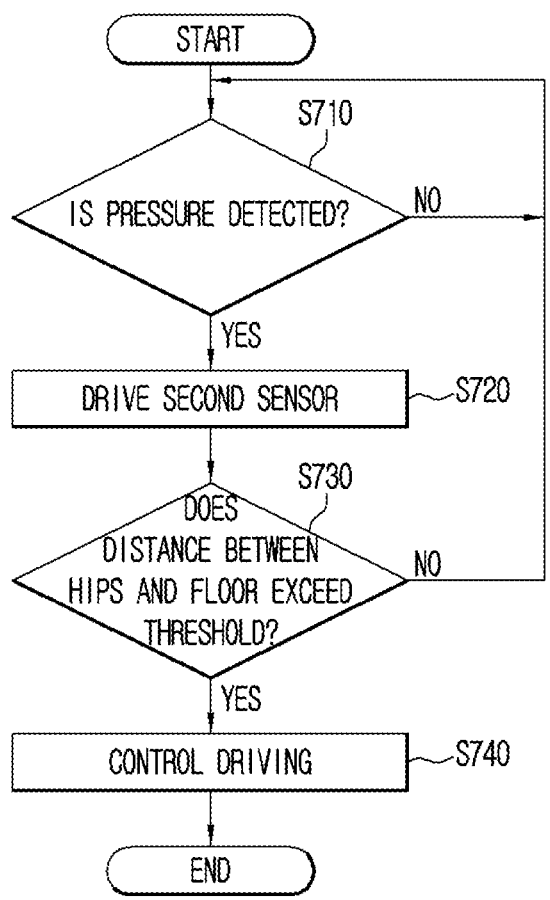
FIG. 7 is a flowchart sequentially illustrating a control method of a walking assistance robot in accordance with some example embodiments.
Figure 8:
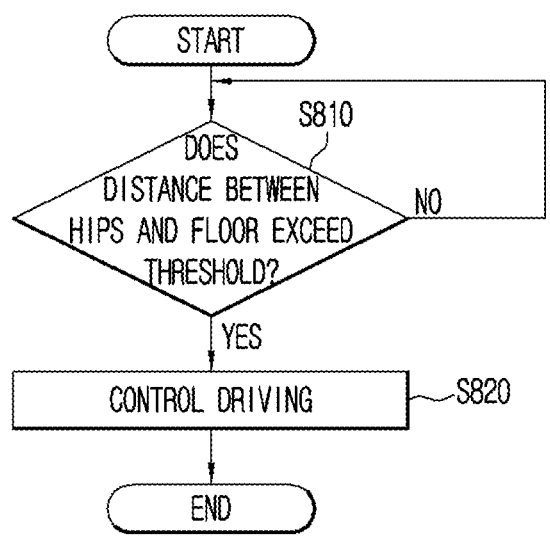
FIG. 8 is a flowchart sequentially illustrating a control method of a walking assistance robot in accordance with some example embodiments.

FIG. 6 is a flowchart sequentially illustrating a control method of a walking assistance robot in accordance with some example embodiments, FIG. 7 is a flowchart sequentially illustrating a control method of a walking assistance robot in accordance with some example embodiments, and FIG. 8 is a flowchart sequentially illustrating a control method of a walking assistance robot in accordance with some example embodiments.

First, a control method of a walking assistance robot in accordance with some example embodiments will be described.

With reference to FIG. 6, the controller 200 judges whether or not pressure is detected through the first sensors 310 provided on the wearer's knees (Operation S610). As a result of judgment, when pressure due to pressing of the wearer's knees is detected through the first sensors 310, the controller 200 judges that the wearer intends to stand up and controls driving to assist corresponding muscular strength (Operation S620).

In general, when a person performs the standing-up motion, the person tends to bend the upper body forward. That is, as exemplarily shown in FIG. 2, the person may bend the upper body forward (state ②) under a sitting state ①, lift the hips (state ③), extend the legs (state ④), and then completely stand (state ⑤). As described above, when a person in the sitting state performs the standing-up motion, the person first bends the upper body down. If the person bends the upper body forward, the person puts the hands on the knees and supports the body with the arms. That is, the person may rise while pressing the knees with the arms. Therefore, in some example embodiments, in order to detect a point in time when the person stands up, the motion of pressing the knees is detected.

When pressure pressing the knees is detected, the controller 200 judges that the wearer intends to stand up and transmits the first control signal to assist corresponding muscular strength to the driving units 110 of the robot unit 100.

Further, a control method of a walking assistance robot in accordance with some example embodiments will be described.

With reference to FIG. 7, the controller 200 judges whether or not pressure is detected through the first sensors 310 provided on the wearer's knees (Operation S710). As a result of judgment, when pressure due to pressing of the wearer's knees is detected through the first sensors 310, the controller 200 transmits a command signal to the second sensors 320 (Operation S720). In some example embodiments, the command signal transmitted to the second sensors 320 may be understood as a signal to indicate measurement of a distance from the wearer's hips to the floor.

Thereafter, the controller 200 judges whether or not the distance measured through the second sensors 320 (i.e., the distance from the wearer's hips to the floor) exceeds a desired value (that may or may not be predetermined) (Operation S730). As a result of judgment, when the distance between the wearer's hips and the floor exceeds the desired value (that may or may not be predetermined), the controller 200 judges that the wearer intends to stand up and transmits the first control signal to assist corresponding muscular strength to the driving units 110 of the robot unit 100 (Operation S740). On the other hand, as a result of judgment, when the distance between the wearer's hips and the floor is below the desired value (that may or may not be predetermined), the controller 200 does not judge that the wearer intends to stand up, and judges again whether or not pressure is detected through the first sensors 310 (Operation S710).

Further, a control method of a walking assistance robot in accordance with some example embodiments will be described.

With reference to FIG. 8, the controller 200 judges whether or not distance information measured through the second sensors 320 (i.e., the distance from the wearer's hips to the floor) exceeds a desired value (that may or may not be predetermined) (Operation S810). As a result of judgment, when the distance between the wearer's hips and the floor exceeds the desired value (that may or may not be predetermined), the controller 200 judges that the wearer intends to stand up and transmits the first control signal to assist corresponding muscular strength to the driving units 110 of the robot unit 100 (Operation S820). On the other hand, as a result of judgment, when the distance between the wearer's hips and the floor is below the desired value (that may or may not be predetermined), the controller 200 does not judge that the wearer intends to stand up, and judges again whether or not the distance measured through the second sensors 320 exceeds the desired value (that may or may not be predetermined) (Operation S810).

As is apparent from the above description, a wearable robot and a control method thereof in accordance with some example embodiments may sense a wearer's intention to stand up through pressure measurement sensors provided on the wearer's knees in consideration of the fact that, when a person stands up, the person presses the knees with the arms, and thus accurately determine when to provide muscular strength assistance.

Further, the wearable robot and the control method thereof in accordance with some example embodiments may more accurately determine when to provide muscular strength assistance using a distance measurement sensor provided on the rear surface of the wearer's waist together with the pressure measurement sensors provided on the wearer's knees.

The methods described above may be written as computer programs and can be implemented in general-use digital computers that execute the programs using a computer-readable recording medium. In addition, a structure of data used in the methods may be recorded in a computer-readable recording medium in various ways. Examples of the computer-readable recording medium include storage media such as magnetic storage media (e.g., ROM (Read-Only Memory), RAM (Random-Access Memory), USB (Universal Serial Bus), floppy disks, hard disks, etc.) and optical recording media (e.g., CD-ROMs (Compact Disc Read-Only Memories) or DVDs (Digital Video Discs)).

In addition, some example embodiments may also be implemented through computer-readable code/instructions in/on a medium (e.g., a computer-readable medium) to control at least one processing element to implement some example embodiments. The medium may correspond to any medium/media permitting the storage and/or transmission of the computer-readable code.

The computer-readable code may be recorded/transferred on a medium in a variety of ways, with examples of the medium including recording media, such as magnetic storage media (e.g., ROM, floppy disks, hard disks, etc.) and optical recording media (e.g., CD-ROMs or DVDs), and transmission media such as Internet transmission media. Thus, the medium may be such a defined and measurable structure including or carrying a signal or information, such as a device carrying a bitstream according to some example embodiments. The media may also be a distributed network, so that the computer-readable code is stored/transferred and executed in a distributed fashion. Furthermore, the processing element could include a processor or a computer processor, and processing elements may be distributed and/or included in a single device.

In some example embodiments, some of the elements may be implemented as a 'module'. According to some example embodiments, 'module' means software-based components or hardware components, such as a field programmable gate array (FPGA) or an application specific integrated circuit (ASIC), and the module may perform certain functions. However, the module is not limited to software or hardware. The module may be configured so as to be placed in a storage medium which may perform addressing, or to execute one or more processors.

For example, modules may include components such as software components, object-oriented software components, class components, and task components, processes, functions, attributes, procedures, subroutines, segments of program code, drivers, firmware, microcodes, circuits, data, databases, data structures, tables, arrays, and variables. Functions provided from the components and the modules may be combined into a smaller number of components and modules, or be separated into additional components and modules. Moreover, the components and the modules may execute one or more central processing units (CPUs) in a device.

Some example embodiments may be implemented through a medium including computer-readable codes/instructions to control at least one processing element of the above-described embodiment, for example, a computer-readable medium. Such a medium may correspond to a medium/media that may store and/or transmit the computer-readable codes.

The computer-readable codes may be recorded in a medium or be transmitted over the Internet. For example, the medium may include a ROM, a RAM, a CD-ROM, a magnetic tape, a floppy disc, an optical recording medium, or a carrier wave such as data transmission over the Internet. Further, the medium may be a non-transitory computer-readable medium. Since the medium may be a distributed network, the computer-readable code may be stored, transmitted, and executed in a distributed manner. Further, for example, the processing element may include a processor or a computer processor, and be distributed and/or included in one device.

Although some example embodiments have been shown and described, it would be appreciated by those skilled in the art that changes may be made in these example embodiments without departing from the principles and spirit of the example embodiments, the scope of which is defined in the claims and their equivalents. For example, while certain operations have been described as being performed by a given element, those skilled in the art will appreciate that the operations may be divided between elements in various manners.

Although some example embodiments are described above with relation to wearable robots for humans and control methods thereof, those skilled in the art will appreciate that some example embodiments may be applied to other types of robots, systems, and control methods, such as wearable robots for animals and control methods thereof, or more general purpose systems and control methods.

While example embodiments have been particularly shown and described, it will be understood by those of ordinary skill in the art that various changes in form and details may be made therein without departing from the spirit and scope of the present invention as defined by the following claims.

What is claimed is:

1. A wearable robot, comprising:
   a robot unit including machinery configured to assist a wearer's muscular strength;
   at least one first sensor configured to be installable on the wearer's knees and configured to detect the wearer's motion of pressing the wearer's knees;
   at least one second sensor configured to measure a distance between the wearer's hips and a floor; and
   a controller configured to,
      judge whether or not the wearer intends to stand up based on information detected using the at least one first sensor and the at least one second sensor,
      transmit a control signal to assist corresponding muscular strength to the robot unit upon judging that the wearer intends to stand up,
      instruct the at least one second sensor to measure the distance between the wearer's hips and the floor when the wearer's motion of pressing the wearer's knees is detected by the at least one first sensor, and
      transmit the control signal to the robot unit when the measured distance exceeds a threshold.

2. The wearable robot according to claim 1, wherein the at least one first sensor comprises a pressure sensor or on/off button.

3. The wearable robot according to claim 1, wherein the robot unit includes a waist wearable unit configured to be worn on a waist of the wearer.

4. The wearable robot according to claim 3, wherein the at least one second sensor is configured to be installable on the waist wearable unit.

5. The wearable robot according to claim 1, wherein the at least one second sensor comprises an ultrasonic sensor or an infrared sensor.

6. A control method of a wearable robot, the method comprising:
   judging whether or not pressure to a wearer's knees is detected;
   measuring a distance between the wearer's hips and a floor, upon judging that the pressure to the wearer's knees is detected;
   judging whether or not the measured distance exceeds a threshold; and
   judging that the wearer intends to stand up and developing assistance to corresponding muscular strength, upon judging that the measured distance exceeds the threshold.

7. A robot, comprising:
   a structure configured to assist a wearer's muscular strength;
   at least one first sensor configured to be installable on the wearer's knees and configured to detect pressure applied to the wearer's knees;
   at least one second sensor configured to measure a distance between the wearer's hips and a floor; and
   a controller configured to,
      judge whether or not the pressure applied to the wearer's knees is detected,
      instruct the at least one second sensor to measure the distance between the wearer's hips and the floor when the pressure applied to the wearer's knees is detected,
      judge whether or not the measured distance exceeds a threshold, and
      transmit a control signal to assist corresponding muscular strength to the structure when the measured distance exceeds the threshold.

8. The robot according to claim 7, wherein the structure comprises at least one support frame.

9. The robot according to claim 7, wherein the structure comprises at least one first support frame and at least one second support frame, and
   wherein the at least one first support frame is operatively connected to the at least one second support frame by a joint.

10. The robot according to claim 9, further comprising:
    a device to measure an angle between the at least one first support frame and the at least one second support frame.

* * * * *